(12) United States Patent
Wilson et al.

(10) Patent No.: US 6,197,001 B1
(45) Date of Patent: Mar. 6, 2001

(54) VASCULAR ACCESS DEVICE

(75) Inventors: Jay Wilson, Portola Valley; Shawn Hanna, Woodside; Jeff Chen, Mountain View; Robert C. Hall, Palo Alto; Teddy Bryant, San Francisco, all of CA (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 08/722,788

(22) Filed: Sep. 27, 1996

(51) Int. Cl.[7] .................................................. A61M 5/178
(52) U.S. Cl. ............................ 604/157; 604/95; 604/164
(58) Field of Search .................................. 128/657, 772; 604/164, 165, 95, 157, 156

(56) References Cited

U.S. PATENT DOCUMENTS

| | | | |
|---|---|---|---|
| 4,068,659 | * 1/1978 | Moorehead | 128/214.4 |
| 4,194,505 | 3/1980 | Schmitz | 128/218 D |
| 4,274,408 | 6/1981 | Nimrod | 128/214.4 |
| 4,417,886 | * 11/1983 | Frankhouser et al. | 604/53 |
| 4,464,171 | 8/1984 | Garwin | 604/53 |
| 4,747,831 | 5/1988 | Kulli | 604/110 |
| 4,894,052 | 1/1990 | Crawford | 604/63 |
| 5,312,361 | 5/1994 | Zadini et al. | 604/165 |
| 5,415,177 | * 5/1995 | Zadini et al. | 128/772 |
| 5,425,718 | * 6/1995 | Tay et al. | 604/165 |
| 5,480,388 | 1/1996 | Zadini et al. | 604/165 |
| 5,527,290 | 6/1996 | Zadini et al. | 604/165 |
| 5,527,291 | 6/1996 | Zadini et al. | 604/165 |
| 5,579,780 | 12/1996 | Zadini et al. | 128/772 |
| 5,665,072 | * 9/1997 | Yoon | 604/164 |
| 5,713,870 | * 2/1998 | Yoon | 604/174 |
| 5,755,709 | * 5/1998 | Cuppy | 604/164 |

FOREIGN PATENT DOCUMENTS 0 577 448 A1    1/1994  (EP) .

* cited by examiner

*Primary Examiner*—Ronald Stright
*Assistant Examiner*—Sharon Finkel
(74) *Attorney, Agent, or Firm*—Eric M. Lee

(57) ABSTRACT

The present invention is directed to a vascular access device for introducing a catheter in a blood vessel using a guide advancing mechanism. The device generally comprises a housing, an introducer needle, a catheter, a guide wire and an actuating means. The introducer needle of the vascular access device is used to penetrate the blood vessel. The actuating means is then initiated and the guide wire is steadily propelled into the blood vessel. Once the guide wire is in place, the catheter, which is concentrically placed over the introducer needle and guide wire, is uncoupled from the vascular access device and guided into the blood vessel by the guide wire.

18 Claims, 9 Drawing Sheets

VASCULAR ACCESS DEVICE

THE FIELD OF THE INVENTION

The present invention is related to a device for facilitating the insertion of vascular catheters. More particularly, the present invention relates to an automatic mechanism for advancing a flexible wire into a blood vessel thus facilitating the proper placement of an associated catheter.

BACKGROUND

During medical treatment, patients often require medication, blood, or fluids. The most efficient way of administering these substances is by depositing them directly into the patient's blood stream where the circulatory system quickly directs the substance to the target tissue or organ. Administering a substance directly into a patient's blood stream is most commonly accomplished by injection with a conventional needle and syringe. During the course of treatment, however, a patient will often require repeated or continuous doses of medications. It will be appreciated that repeated injections with a conventional needle can damage veins or arteries and cause significant discomfort to the patient.

When a patient requires repeated doses of medication or other substances, catheters are commonly employed. A catheter is a device that permits repeated and continuous administration of medication directly into a patient's blood stream, or other region of the body, without repeated injections. In one common configuration, catheters have a hollow tubular cannula and an adapter at the proximal end. The cannula of the catheter is inserted into the vein or artery of a patient while the catheter adapter remains outside the patient. The adapter permits repeated and continuous access to the patient's vascular system thus obviating the need for repeat injections.

In certain situations it is necessary to have access to the arteries of a patient. Generally this is necessary in order to monitor blood pressure and to take samples of arterial blood. In any event, in certain situations it is desirable to have the ability to repeatedly access an artery without making multiple needle punctures of the artery. In these situations it is often desirable to inert an arterial catheter.

There are many known devices and methods for introducing a catheter into a blood vessel. One such device uses an "inside-the-needle" configuration. As its name implies, this device has a catheter coaxially located within a hollow introducer needle. The patient's blood vessel is pierced with an introducer needle. Once the needle is within the patient's blood vessel, the catheter is manually advanced into the patient's blood vessel so that the desired length of the catheter has been inserted. The needle is then removed leaving the catheter in place. Thereafter, an adapter is attached to the proximal end of the catheter so that medication or other substances may be administered.

Another device used to introduce a catheter into a patient's blood vessel also uses an introducer needle to penetrate the blood vessel but in an "over-the-needle" configuration. In this arrangement, the catheter is coaxially placed over the needle. Once the needle is within the patient's blood vessel, the catheter is advanced over the introducer needle until the desired length of the catheter has been inserted. The needle is simultaneously withdrawn and discarded leaving the catheter in place. Because the catheter is located over the needle, an adapter need not be attached to the catheter after placement of the catheter in the blood vessel, but can be attached to the catheter prior to placement.

It will be appreciated that for maximum comfort to the patient, catheters should be constructed of a flexible pliable material. The more pliable the material, however, the more difficult it is to insert the catheter into the blood vessel. The catheter has a tendency to kink making its insertion difficult, and in many cases impossible. This is especially true for catheters that will be placed in an artery. As a result, vascular catheters typically employ a thin wire called a guide wire which can be advanced into the artery to provide a path for the catheter to follow while the catheter is positioned within the blood vessel.

One such catheter uses an introducer needle to penetrate the patient's artery. Once in place, a guide wire which is disposed within the introducer needle is manually advanced into the artery. The catheter is then detached and advanced from the introducer needle along the guide wire which guides the catheter within the artery. The introducer needle and the guide wire are then removed leaving the catheter in place.

Unfortunately, this device and method compromise stability by requiring the clinician to hold the catheter unit with one hand while the guide wire is manually advanced with the other. While the guide wire is being manually advanced, the needle within the artery is subject to movement making it difficult to steadily insert the guide wire.

Several automatic and semiautomatic devices and methods for advancing the guide wire are known in the art. One such device requires the clinician to carefully pierce the patient's skin with the introducer needle. Once the skin is punctured, but before the introducer needle pierces the blood vessel, a vacuum is created by manually extending a plunger or similar apparatus. Subsequently, the introducer needle is advanced further until the blood vessel is penetrated. Upon penetration, the vacuum in the chamber is broken and the guide wire is advanced by one of several different mechanisms. Alternatively, once the vacuum is broken and blood is visible in the chamber, the operator can manually initiate the guide wire advance mechanism.

Like the manual devices, these automatic and semiautomatic devices require the clinician to steadily hold the catheter unit with one hand while the plunger is extended to create a vacuum. In addition, these devices require great skill on the part of the clinician. If the blood vessel is penetrated before a vacuum is created, the guide wire will not automatically advance. Moreover, if the guide wire fails to properly advance neither the automatic nor the semiautomatic mechanisms permit the guide wire advance mechanism to be reset and reinitiated.

It will be appreciated that it would be an advancement in the art to provide a vascular access device that automatically advances a guide wire into a blood vessel. It would be a further advancement in the art if the guide wire could be advanced at a steady and a consistent rate and the device reset if necessary. It would be yet another advancement in the art if the flexible wire could be advanced with one hand without requiring the operator to remove one hand from the device.

Such a vascular access device is disclosed and claimed herein.

BRIEF SUMMARY AND OBJECTS OF THE INVENTION

The present invention is directed to a vascular access device for introducing a catheter into a blood vessel. The present invention uses an introducer needle to penetrate the patient's skin and blood vessel. Once in place, the operator can manually trigger an activating means located within the device. A guide wire is then propelled past the tip of the needle and into the blood vessel. A catheter concentrically located over the introducer needle can then be advanced along the introducer needle and guided into the blood vessel by the guide wire. Once secure in the blood vessel, the introducer needle and the guide wire are removed leaving the catheter in place in the patient.

In one preferred embodiment, the vascular access device comprises a housing, an introducer needle, a guide wire, and an actuating mechanism, together with an associated catheter. The housing is generally cylindrical and accommodates the actuating mechanism disposed within its hollow center. The proximal end of the housing is sealed by a cap. The cap may be attached to the housing by a variety of means including threads or resilient means. The distal end of the housing defines a nose which may be constructed as a single piece integral with the housing, or alternatively may be constructed separately and attached. The proximal end of the introducer needle is secured within the nose with the distal end of the introducer needle having a beveled tip for penetrating a blood vessel.

The typical catheter used in connection with the device is comprised of a hollow cannula that fits concentrically over the introducer needle. The proximal end of the cannula is connected to an adapter that fits over the nose of the housing and is attached by friction engagement. It will be appreciated that the specific shape of the catheter adapter and housing nose are not critical to the invention. The catheter adapter, for example, may be compatible with an IV administration set that provides the fluid to be administered to the patient.

The guide wire is disposed within the hollow introducer needle and extends through the nose and into the cavity of the housing. As will be explained in greater detail below, the proximal end of the guide wire is in communication with the actuating mechanism at the rear of the housing. The guide wire is longer than the introducer needle. However, when the vascular access device is in a locked position (i.e., before the advancement of the guide wire) the distal tip of the guide wire preferably does not extend beyond the beveled tip of the introducer needle. In the presently preferred embodiments of the device, the guide wire is flexible but also sufficiently rigid to prevent kinking as it is inserted into the blood vessel. It will be appreciated by one skilled in the art that the exact flexibility and rigidity will depend on the particular use and location where the catheter is to be inserted.

The actuating mechanism is generally disposed within the rear of the housing and generally comprises a resilient member, a disk, and a trigger. The proximal end of the resilient member is attached to the housing cap and the distal end of the resilient member is attached to the disk. Also attached to the disk is the proximal end of the guide wire. When the vascular access device is in a first locked position, the resilient member and disk are compressed toward the rear of the housing. The trigger engages the disk preventing the resilient member from expanding and the guide wire from advancing.

In use, a clinician first pierces the skin and penetrates the patient's blood vessel with the introducer needle. Once the introducer needle is in the lumen of the blood vessel, the trigger of the actuating mechanism is manually depressed. Depressing the trigger causes the end of the trigger to disengage from the disk permitting the resilient member and disk to expand axially through the interior of the housing. The expansion of the resilient member and disk propels the distal end of the guide wire beyond the beveled tip of the introducer needle and into the blood vessel. Thereafter, the catheter adapter is removed from the housing nose and the catheter is slid along the introducer needle and guide wire. The guide wire guides the catheter until the catheter is secured within the blood vessel. Once the catheter is in place, the introducer needle and guide wire are removed. The catheter cannula remains within the lumen of the patient's blood vessel while the catheter adapter remains outside the patient, facilitating the introduction of medication, fluids, blood and other substances.

These and other objects and advantages of the present invention will become more fully apparent by examination of the following description of the preferred embodiments and the accompanying drawings.

BRIEF DESCRIPTION OF THE DRAWINGS

A more particular description of the invention briefly described above will be rendered by reference to the appended drawings. Understanding that these drawings only provide information concerning typical embodiments of the invention and are not therefore to be considered limiting of its scope, the invention will be described and explained with additional specificity and detail through the use of the accompanying drawings, in which.

DETAILED DESCRIPTION OF THE PREFERRED EMBODIMENTS

Figure 1:
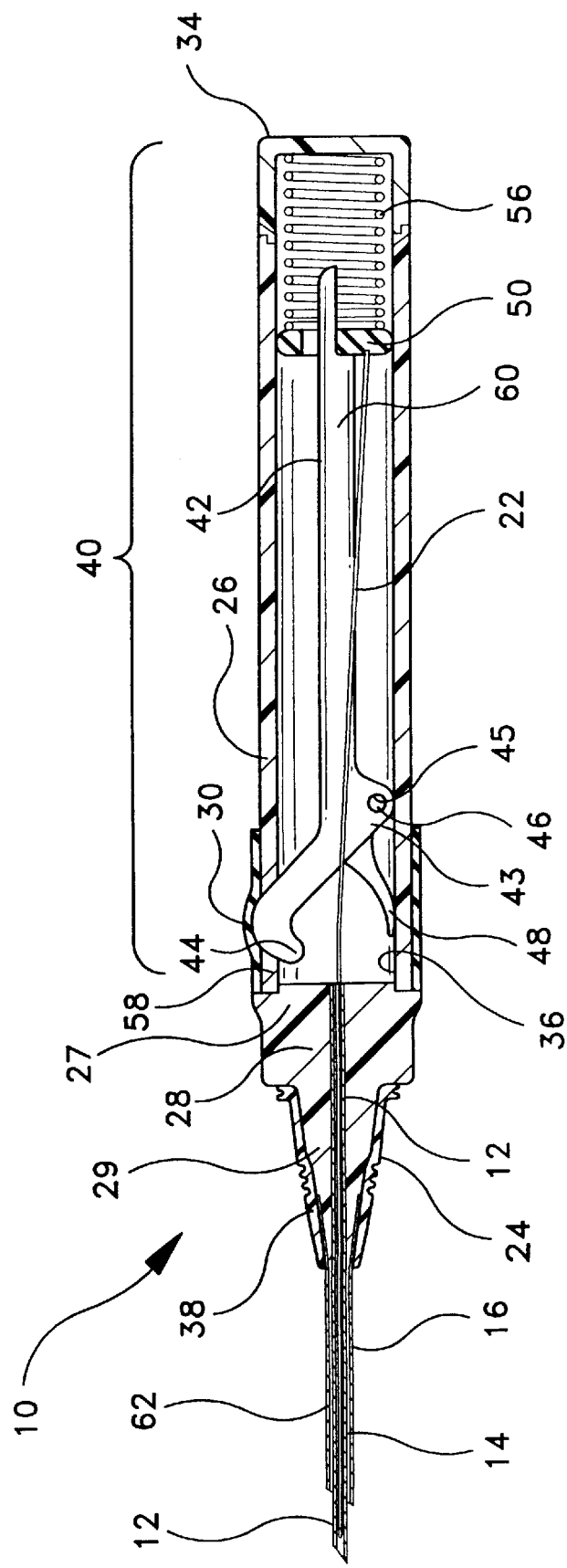
FIG. 1 is a cross sectional view of the vascular access device of the present invention in the locked position before the advancement of the guide wire.

The present invention is a vascular access device for inserting a catheter into a blood vessel. Generally, the vascular access device comprises a hollow introducer needle, a catheter concentrically placed over the introducer needle, an actuating means, and a guide wire running from the actuating means to the introducer needle. A catheter is positioned over the needle prior to operation of the device. In practice, the introducer needle is inserted into a blood vessel. Once in place, the actuating means is manually initiated and the guide wire is advanced beyond the end of the introducer needle and into the blood vessel. Thereafter, the catheter is uncoupled from the introducer needle and slid along the introducer needle and guide wire until the catheter is secured within the blood vessel. Finally, the introducer needle and guide wire are removed leaving the catheter in the blood vessel. Accordingly, the vascular access device of the present invention permits the operator to easily and steadily advance the guide wire into the patient's blood vessel using only one hand.

Reference is now made to the figures wherein like parts are designated by like numerals throughout. One embodiment of the vascular access device of the present invention is designated 10 in FIG. 1. The vascular access device 10 generally comprises a generally cylindrical housing 26, an introducer needle 12, a catheter 16, an actuating mechanism 40, and a guide wire 22. The basic components of the device housed within housing 26 include spring 56 which is held in place by disk 50, the operation of which will be discussed in additional detail below. Also contained within housing 26 is the actuating mechanism 40 which allows for selective release of spring 56. Running from disk 50 through the interior of housing 26 and out into the interior of needle 12 is guide wire 22. The primary purpose of device 10 is to aid in the placement of guide wire 22 within a blood vessel, and the subsequent placement of catheter 16.

As illustrated in FIG. 1, housing 26 is generally cylindrical and has a cylindrical cavity 36. The rear end of housing 26 has a cap 34 that seals cavity 36. Cap 34 may be attached by a variety of means including molding in place, friction engagement, or threaded attachment. Housing 26 is preferably constructed of a rigid plastic. One skilled in the art will appreciate, however, that housing 26 may be constructed of other rigid materials. Similarly, the shape of housing 26 may be varied to meet specific needs. Any shape that allows the operator firmly and comfortably to grip the vascular access device 10 is within the scope of the invention.

Housing 26 also has a slit 58 that, as will be explained in more detail below, accommodates trigger 42 of actuating mechanism 40. Slit 58 is covered by a plastic or rubber jacket 30 which wraps around the outer circumference of housing 26. Jacket 30 also facilitates the gripping of vascular access device 10 by the operator.

The distal portion of housing 26 includes a nose portion 28. In a preferred embodiment, nose 28 and housing 26 are molded from a single piece of material. However, nose 28 and housing 26 may be constructed as separate segments and attached by a variety of means, including adhesive or threaded engagement. Moreover, nose 28 and housing 26 may be constructed of the same or different materials.

Attached to nose 28 is introducer needle 12. As illustrated in FIG. 1, introducer needle 12 is hollow or cannulated throughout its entire length and has a beveled tip 18 at its distal end used to penetrate the skin and blood vessel. In FIG. 1, the proximal end of introducer needle 12 runs through the center of nose 28 and spans its entire length from cavity 36. It is not critical, however, that introducer needle 12 span the entire length of nose 28. The proximal end of introducer needle 12 may, for example, be attached only to the distal end 29 of nose 28. In that case, a hole must be bored through the proximal end 27 of nose 28 providing an opening from cavity 36 of housing 26 to introducer needle 12 so that the guide wire 22 can travel through the nose 28.

FIG. 1 also illustrates catheter 16 attached to nose 28 by means of friction engagement between nose 28 and catheter adapter 38. Catheter 16 has a tip 14, a cylindrical hollow cannula 62, and an adapter 38. Catheter 16 fits concentrically over introducer needle 12 and nose 28. Adapter 38 is configured such that it couples with nose 28 by friction engagement. However, other engagement methods, including threads and Luer lock mechanisms, may be employed to secure catheter 16 to nose 28. The overall length of catheter 16 is such that when catheter 16 is fastened to nose 28, beveled tip 18 of introducer needle 12 extends beyond tip 14 of catheter 16.

Figure 2:
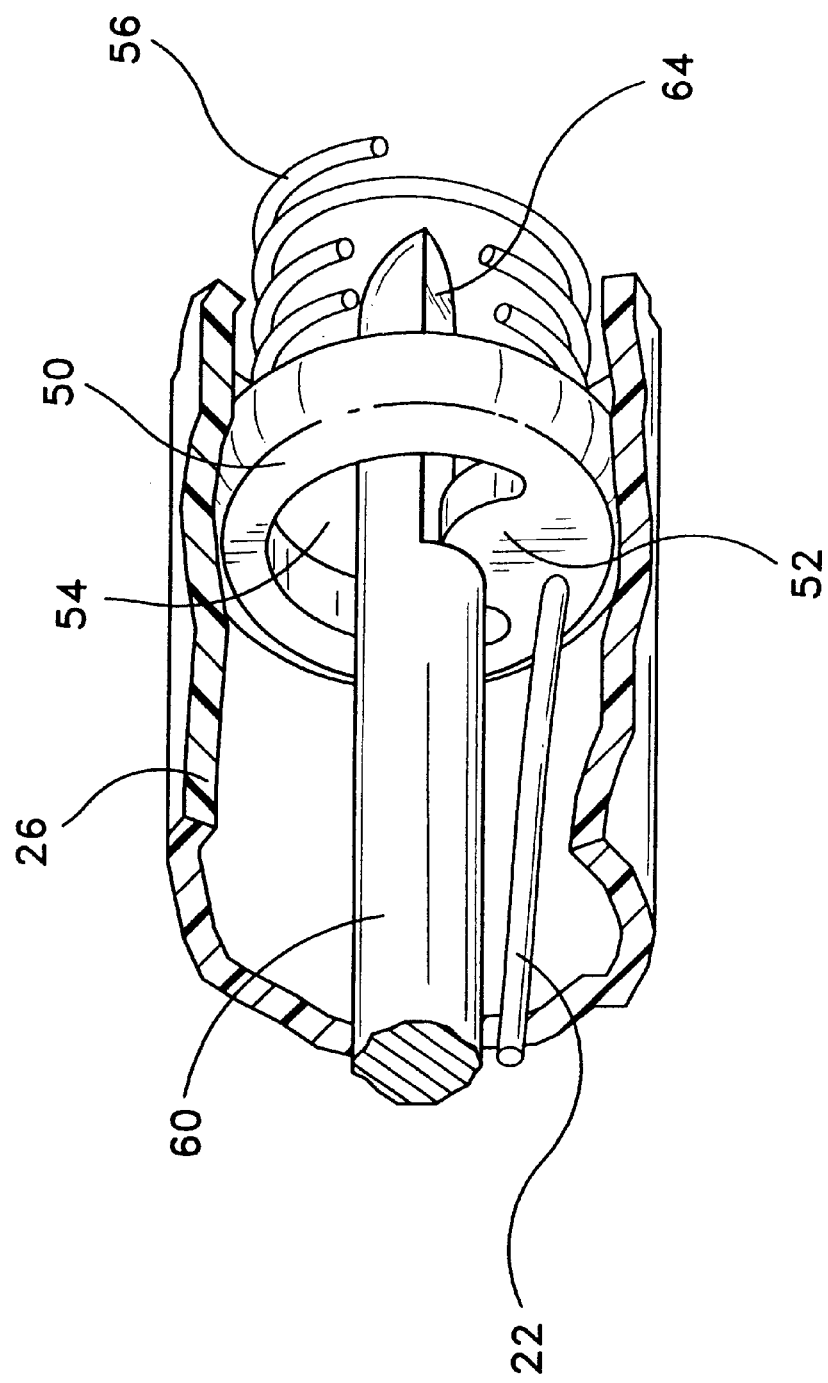
FIG. 2 is a partially cut-away perspective view of the locking mechanism before the advancement of the guide wire.

With continued reference to FIG. 1, vascular access device 10 has an actuating mechanism 40. Actuating mechanism 40 is disposed within cavity 36 toward the proximal end of housing 26. Actuating mechanism 40 generally comprises a trigger 42, a disk 50, and a spring 56. In the illustrated embodiment, spring 56 is a coil spring with a diameter less than the diameter of cavity 36. At the proximal end of housing 26, spring 56 is attached to cap 34. At the opposite end of cap 34, spring 56 is attached to disk 50. Spring 56 may be attached to or rest against cap 34 and disk 50. The diameter of disk 50 is preferably greater than the diameter of spring 56, but less than the diameter of cavity 36 such that disk 50 can move freely through the interior of cavity 36. As best illustrated in FIG. 2, disk 50 has a U-shaped aperture 54 that carves out a disk tab 52. As will explained below, disk tab 52 serves to hold spring 56 in abeyance when the actuating mechanism is in a locked position prior to the advancement of guide wire 22 into the patient's blood vessel.

Attached to disk 50 is a guide wire 22. As shown in FIG. 1, the proximal end of guide wire 22 penetrates disk 50 and is affixed by friction engagement, adhesive, or other engagement mechanism. From disk 50, guide wire 22 extends forwardly through cavity 36, nose 28, and introducer needle 12. Before initiating the actuating mechanism, the distal tip of guide wire 22 is disposed within introducer needle 12 but does not extend beyond beveled tip 18.

Figure 3:
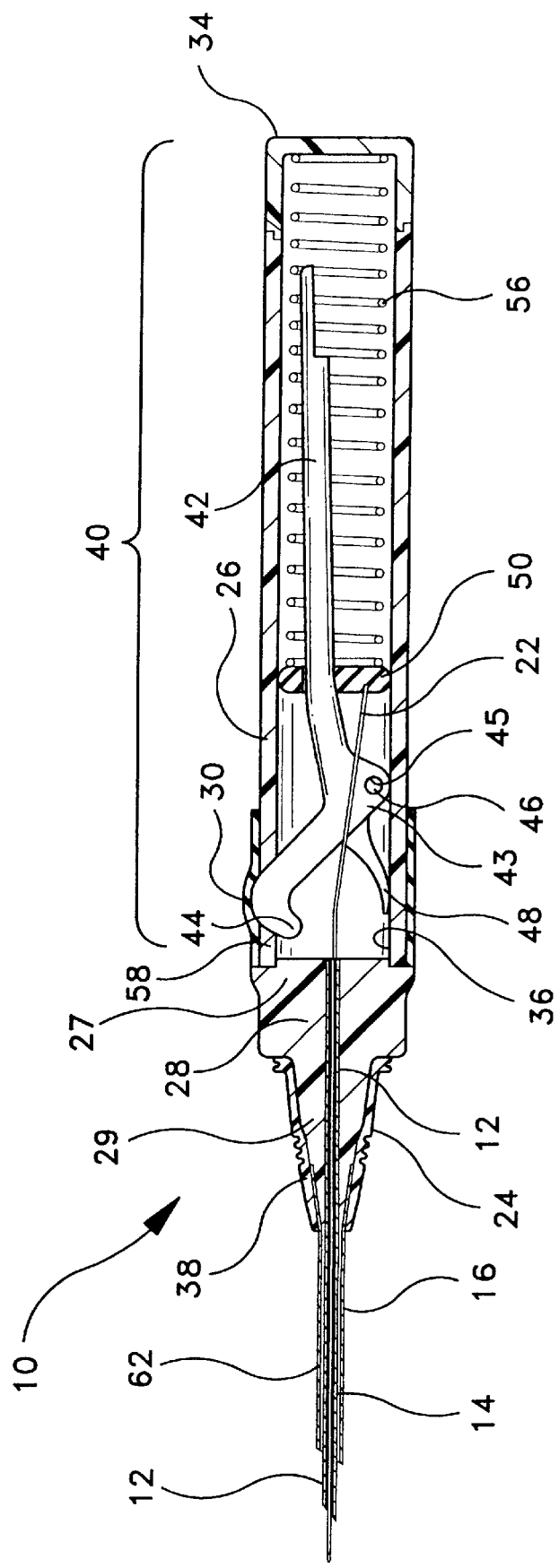
FIG. 3 is a cross sectional view of the vascular access device of the present invention in the unlocked position with the spring expanded and the guide wire fully advanced.

Trigger 42 engages disk 50 and spring 56. In the illustrated embodiment, trigger 42 is a sickle-shaped element with a trigger shaft 60 at its proximal end and a trigger arm 44 at its distal end. Near the center of trigger 42, between trigger shaft 60 and trigger arm 44, is a bell-shaped boss 43 with a bore 45 running perpendicular to trigger 42. Trigger 42 may be constructed of any material known in the art, such as plastic or metal, and may be flexible as illustrated in FIG. 3, or rigid.

As illustrated in FIG. 1, trigger 42 is pivotally attached to housing 26 by a trigger pin 46. Trigger pin 46 traverses the width of cavity 36, passes though bore 45 of boss 43 and is affixed at either end to housing 26. As such, trigger pin 46 secures trigger 42 to housing 26. The diameter of bore 45, however, is larger that the diameter of pin 46. Trigger pin 42, therefore, can freely pivot about trigger pin 46.

As depicted in FIG. 1 and FIG. 2, trigger shaft 60 extends proximally from trigger pin 46. The proximal end of trigger shaft 60 has a notch 64 that forms a seat 68. In the locked position, spring 56 is compressed toward the rear of cavity 36 and notch 64 extends through aperture 54 of disk 50. Spring 56 is kept from expanding and advancing axially along cavity 36 by disk tab 52 which overlaps and is biased against seat 68 of trigger 42.

The relative position of disk tab 52 and seat 68 is maintained by a trigger spring 48 near the distal end of trigger 42. Trigger spring 48 is in communication with trigger 42 and provides resistance against trigger arm 44. The resistance may be provided by means of a spring or any other resilience means well known in the art. The action of trigger spring 48 forces trigger arm 44 to extend through slit 58 of housing 26 and against plastic cover 30. The force of trigger arm 44 causes cover 30 to expand, allowing trigger arm 44 to protrude through slit 58 of housing 26. Simultaneously, the action of trigger spring 48 causes trigger 42 to pivot about trigger pin 46 and boss 43, urging seat 68 to overlap disk tab 52. Additionally, the resistance of spring 56 against disk 50 causes significant friction between disk tab 52 and seat 68 further ensuring that the two remain in an overlapped position.

While disk tab 52 and seat 68 of trigger 60 are overlapped, spring 56 cannot advance axially along cavity 36 and guide wire 22 remains within introducer needle 12. To advance guide wire 22 beyond beveled tip 18, the clinician depresses the portion of trigger arm 44 that protrudes through slit 58 of housing 26. This causes trigger 42 to pivot about trigger pin 48 and forces trigger shaft 60 away from disk tab 52 of disk 50. As trigger shaft 60 moves away from disk tab 52, seat 68 of trigger shaft 60 slides off disk tab 52.

Figure 4:
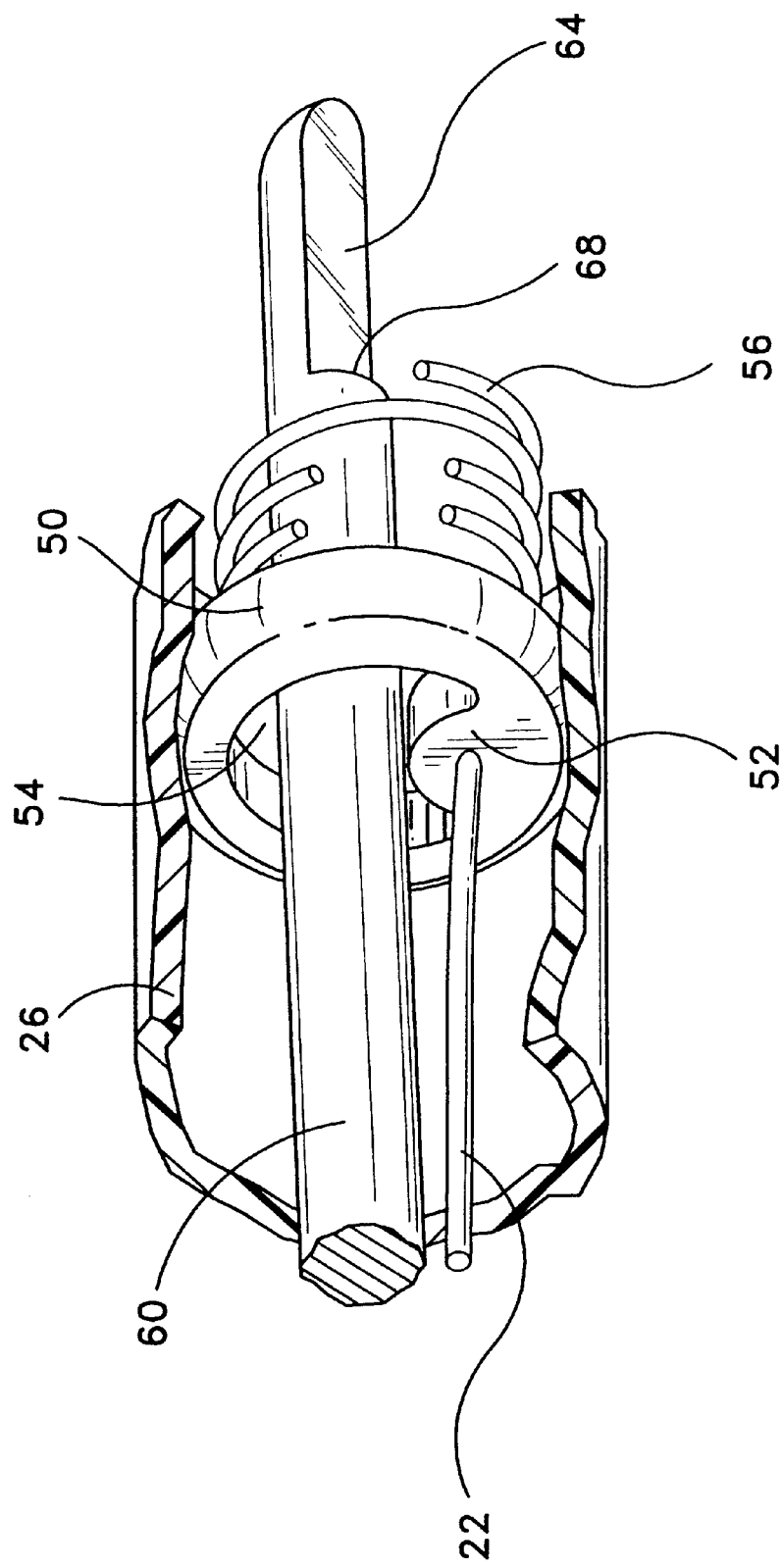
FIG. 4 is a partially cut-away perspective view of the locking mechanism following advancement of the guide wire.

As best illustrated in FIGS. 3 and 4, when seat 68 no longer overlaps disk tab 52, spring 56 can expand and advance disk 50 through cavity 36. As spring 56 expands, trigger shaft 60 passes through aperture 54 of disk 50. As a result of the expansion of spring 56 and the advancement of disk 50, guide wire 22 is propelled past the beveled tip 18 of introducer needle 12. Disk 50 and guide wire 22 come to rest when spring 56 is fully extended or disk 50 is delimited by boss 43. It will be appreciated by one skilled in the art that the speed and force at which guide wire 22 is advanced is directly proportional to the force exerted by spring 56. Thus, depending on the precise location where catheter 16 is being inserted, the force at which guide wire 22 is extended may be tailored by choosing the size and resilient force of spring 56.

In practice, while in the locked position, introducer needle 12 is used to pierce the skin and penetrate the blood vessel. Once in the blood vessel, actuating mechanism 40 is initiated by depressing trigger arm 44 through plastic cover 30. The force against the trigger arm 44 causes trigger 42 to pivot about trigger pin 46 disengaging seat 68 from disk tab 52. This permits spring 56 to expand thus propelling disk 50 axially along cavity 36 toward introducer needle 12. As a result, guide wire 22 which is attached to disk 50 advances beyond beveled tip 18 of introducer needle 12 and into the blood vessel. Guide wire 22 also substantially prevents back bleeding through introducer needle 12. Should guide wire 22 fail to fully advance for any reason, the clinician can reset actuating mechanism 40 by disengaging cap 34 from housing 26 and pulling cap 34 proximally until disk 50 reengages seat 68 of trigger 42. Cap 34 can then be reattached to housing 26 and actuating mechanism 40 can be reinitiated.

While holding housing 26, the operator uncouples catheter 16 from nose 28 and slides it along introducer needle 12 and guide wire 22 until the desired length of cannula 62 of catheter 16 is within the blood vessel. Once in place, the operator holds catheter 16 in place while slowly retracting housing 26, introducer needle 12, and guide wire 22. Catheter 16 can then be used to administer, medication, or other fluids.

Figure 5:
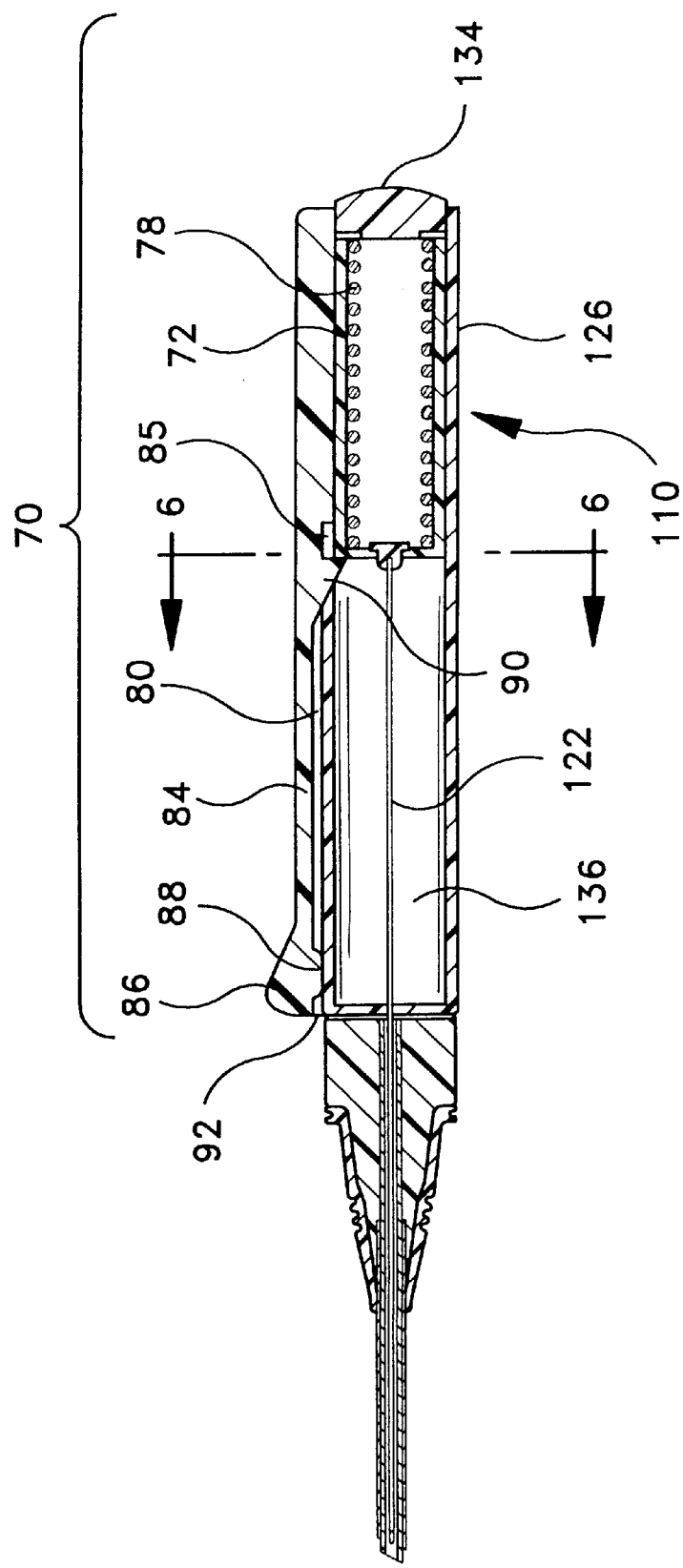
FIG. 5 is a cross sectional view of an alternative embodiment of the vascular access device of the present invention in the locked position before the advancement of the guide wire.

FIG. 5 illustrates an alternative embodiment of the present invention employing an alternative activating means. In FIG. 5, vascular access device 110 has an actuating mechanism 70 generally comprising a plunger 72, a spring 78 and a lever 84. When actuating mechanism 70 is in a locked position before the advancement of guide wire 122 into the blood vessel, plunger 72 is disposed toward the proximal end of cavity 136 of housing 126. Plunger 72 is cylindrical with a diameter smaller than the diameter of housing 126 thus permitting it to move axially within cavity 136.

Figure 6:
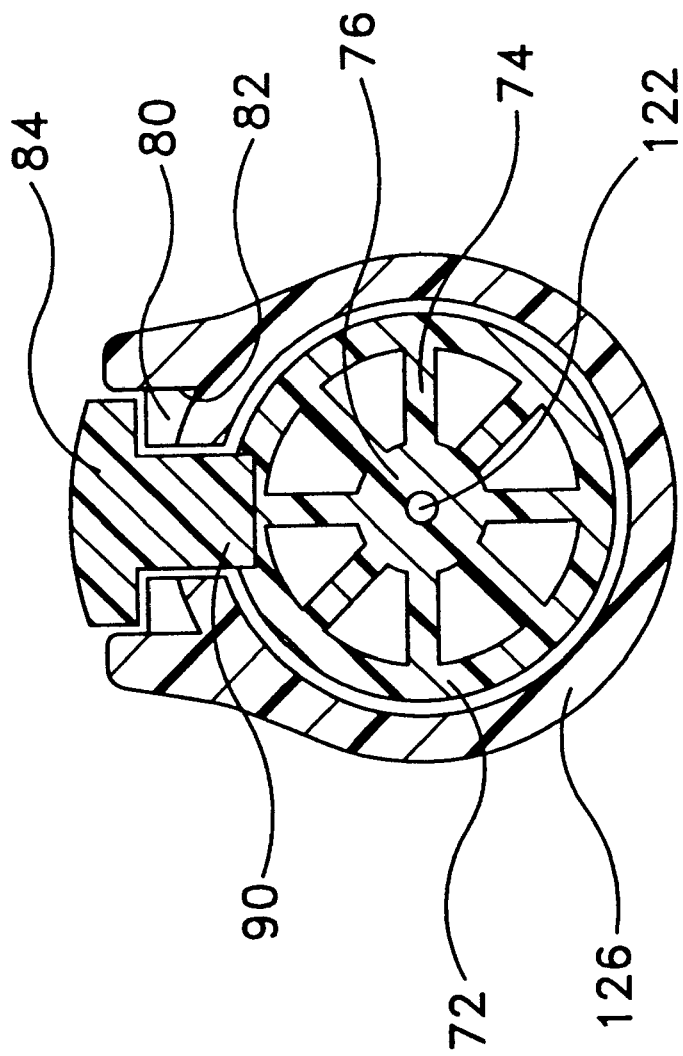
FIG. 6 is a cross sectional view taken along line 6—6 illustrated in FIG. 5.

As best illustrated in FIG. 6, the distal face of plunger 72 has a plurality of spokes 74 and a hub 76. Spokes 74 are evenly spaced and converge on hub 76 in the center of the plunger face. Plunger 72, spokes 74 and hub 76 may be molded from a single material or molded separately and assembled, for example, using adhesive, threaded or friction engagement. Guide wire 122 is attached to the center of hub 76 by adhesive, threaded or friction engagement and extends distally from hub 76 through cavity 136 and into introducer needle 112. Spokes 74 may be configured such that as plunger 72 advances distally through cavity 136, spokes 74 cause plunger 72 and guide wire 122 to spiral. The spiral motion of guide wire 122 assisting its entry into the blood vessel.

Disposed with plunger 72 is coiled spiral spring 78. As will be explained further below, in its fully extended state, spring 78 is longer than plunger 72 so that it is capable of propelling plunger 72 distally when actuating mechanism 70 is initiated. The proximal face of plunger 76 is open allowing spring 78 to contact cap 134 of housing 126. When the vascular access device is in a locked position, spring 78 is compressed toward the rear of housing 126 delimited proximally by cap 134 and distally by spokes 74 of plunger 72. Moreover, it will be appreciated by one skilled in the art that the maximum compressed state of spring 78 is dictated by the length of plunger 72. Thus, depending on the precise location where catheter 116 is to be inserted, the length and force with which guide wire 122 is extended into the blood vessel may be tailored by choosing, not only the size and resilience of spring 78, but also the length of plunger 72. For example, the combination of a short plunger and a highly resilient spring will cause guide wire 122 to be advanced a greater distance and with greater force into the blood vessel.

With continued reference to FIGS. 5 and 6, housing 126 has a recess 80 and a channel 82. Together, recess 80 and channel 82 create an opening through housing 126 into cavity 136. As illustrated in FIG. 5, channel 82 extends the entire length of recess 80. It will be appreciated by one skilled in the art, however, that channel 82 need only be large enough to accommodate pawl 90. When actuating mechanism 70 is in a locked position, recess 80 and channel 82 extend from the distal end of housing 126 near nose 128 proximally beyond the distal face of plunger 72. Lever 84 rests on top and extends the entire length of housing 126. Toward the proximal end of housing 126, from the proximal end of recess 80 to cap 134, lever 84 is attached to housing 126 by adhesive engagement or other means well known in the art. At the distal end of housing 126, lever 84 rests within, but is not attached to, recess 80.

Lever 84 is made of a resilient material such as plastic or metal and has a notch 85 and a tab 88. Notch 85 is adjacent to where lever 84 is attached to housing 126. As will explained below, notch 85 facilitates the bending of lever 84 during actuation of the vascular access device 110. Tab 88 is at the distal end of lever 84. The width of tab 88 is less than recess 80 but greater than channel 82, thus preventing the distal end of lever 84 from passing through channel 82 into cavity 136 of housing 126. The height of tab 88 is such that when tab 88 is resting over channel 82, lever 84 is flush with housing 126 and level with the proximal end of lever 84.

Lever 84 also has a wire release button 86 at its distal end and a release pawl 90 near the proximal end of recess 80.

Wire release button 86 extends above recess 80 of housing 126 for easy access and gripping by the clinician. Release pawl 90 of lever 84 projects below recess 80 and channel 82 and into cavity 136 of housing 126. When actuating mechanism 70 is in a locked position, release pawl 90 overlaps the distal face of plunger 72. The resilient force of spring 78 drives plunger 72 against release pawl 90 which urges wire release button 86 against abutment 92 thus preventing spring 78 from expanding and plunger 72 from advancing distally along cavity 136.

In practice, while in the locked position, introducer needle 112 is inserted into the blood vessel. Once in the blood vessel, the clinician initiates actuating mechanism 70 by gripping wire release button 86 and applying force proximally against the resilient force of spring 78 and away from abutment 92. When wire release button 86 is no longer in contact with abutment 92, and with continued pressure against spring 78, the clinician pulls the wire release button 86 up and away from housing 26. The upward force causes the distal end of lever 84 to bend about notch 85. As lever 84 bends upward away from housing 126, release pawl 90 moves out of cavity 136 and away from plunger 72. When release pawl 90 and plunger 72 no longer overlap, the resilient force of spring 78 against cap 134 advances plunger 72 distally along cavity 136, propelling guide wire 122 past beveled tip 118 of introducer needle 112 and into the patient's blood vessel. As plunger 72 advances, spokes 74 cause plunger 72 and guide wire 122 to spiral facilitating the entry of guide wire 122 into the blood vessel. The openings between spokes 74 in the distal face of plunger 72 allow blood to pass through plunger 72 as it advances preventing the blood from being reintroduced into the patient's blood vessel. Plunger 72 comes to rest when the distal face of plunger 72 contacts the distal end of housing 126. Once guide wire 122 is in position within the patient's blood vessel, catheter 116 is inserted and guide wire 122 and introducer needle 112 are removed as explained above.

Figure 7:
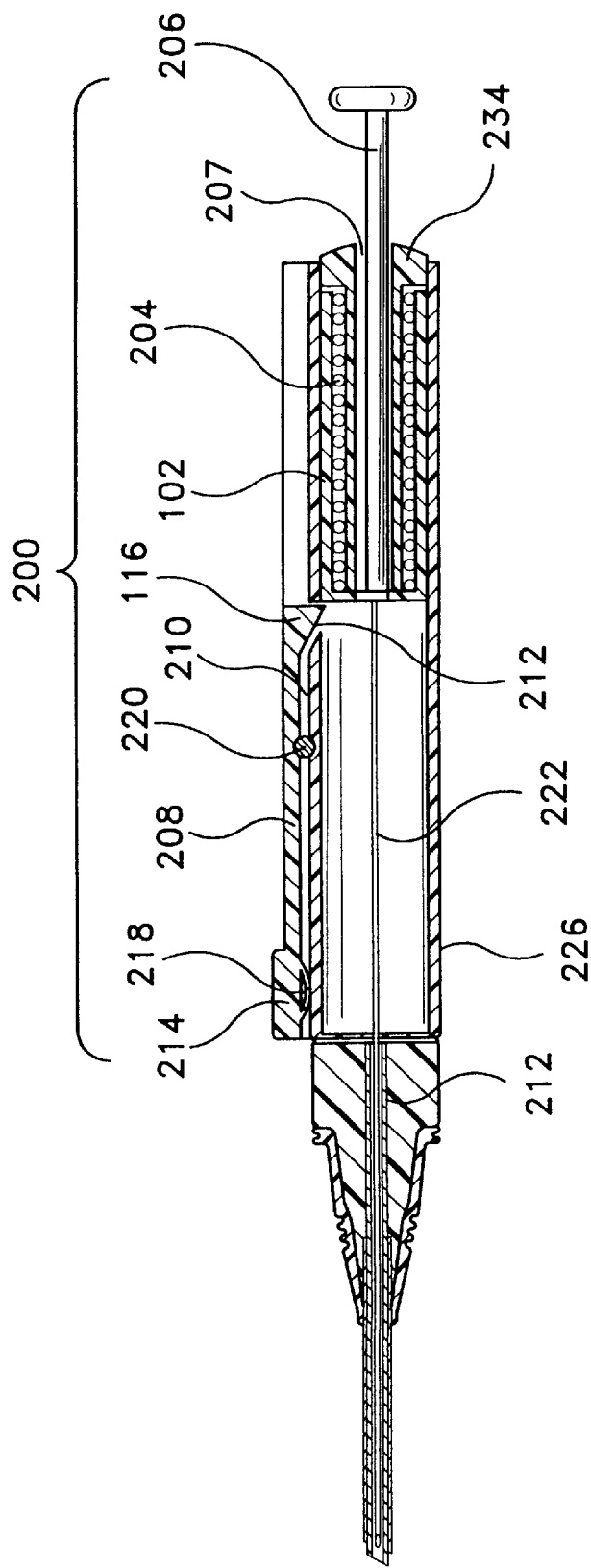
FIG. 7 is a cross sectional view of an alternative embodiment of the vascular access device of the present invention in the locked position before the advancement of the guide wire.

FIG. 7 illustrates an alternative guide wire advancement mechanism for vascular access device 210 of the present invention. In FIG. 7, vascular access device 210 has an actuating mechanism 200 generally comprising a plunger 202, a spring 204, a lever 208 and optionally a handle 206. Plunger 202, spring 204 and guide wire 222 are configured as in FIG. 6 except that a handle 206 is attached to the distal face of plunger 202. Handle 206 can be attached to the distal face of plunger 202 by a variety of means, included adhesive, threaded, or friction engagement. From the distal face of plunger 202, handle 206 extends through the center of spring 204 and opening 207 in cap 234. Guide wire 222 is attached to the distal face of plunger 202 and extends distally through cavity 236 and introducer needle 212.

The top of housing 226 has a recess 210. When actuating mechanism 200 is in a locked position prior to the advancement of guide wire 222, recess 210 extends from the distal end of housing 226 near nose 228 proximately to the distal face of plunger 202. Inset in recess 210 is lever 208 comprising a wire release button 214, release pawl 216, return spring 218 and fulcrum 220. Lever 208 is attached to housing 226 by fulcrum 220. The exact means by which fulcrum 220 attaches lever 208 to housing 226 is not critical to the invention. Threaded, adhesive or friction engagement, or any combination thereof, may be employed provided the engagement permits lever 208 to pivot about fulcrum 220.

With continued reference to FIG. 7, lever 208 is flush with housing 226 except for wire release button 214 which, for reasons that will be explained in further detail below, extends above recess 210. Release pawl 216 projects below recess 210 into cavity 236 through release pawl hole 212 in housing 226. When actuating mechanism 200 is in a locked position, release pawl 216 overlaps plunger 202 preventing it from advancing distally through cavity 236. The resilient force of return spring 218 against housing 226 causes lever 208 to pivot about fulcrum 220 ensuring that release pawl 216 remains engaged with plunger 202.

In practice, if vascular access device 210 is not in a locked position, the clinician first pulls handle 206 proximately until the distal face of plunger 202 is beyond release pawl hole 212 and engages release pawl 216. Once in a locked position, introducer needle 212 is inserted into the blood vessel. The clinician then initiates actuating mechanism 200 by depressing the portion of wire release button 214 which extends above recess 210 of housing 226. The downward force on wire release button 214 against return spring 218 causes lever 208 to pivot about fulcrum 220 driving release pawl 216 out of cavity 236 through release pawl hole 212 and away from the distal face of plunger 202. When release pawl 216 is completely out of cavity 236 and no longer overlapping the distal face of plunger 202, the resilient force of spring 204 against cap 234 advances plunger 202 distally along cavity 236. As plunger 202 advances guide wire 222 is propelled past beveled tip 218 of introducer needle 212 and into the patient's blood vessel. Once guide wire 222 is in position within the patient's blood vessel, catheter 216 is inserted and guide wire 222 and introducer needle 212 are removed as explained above.

Figure 8:
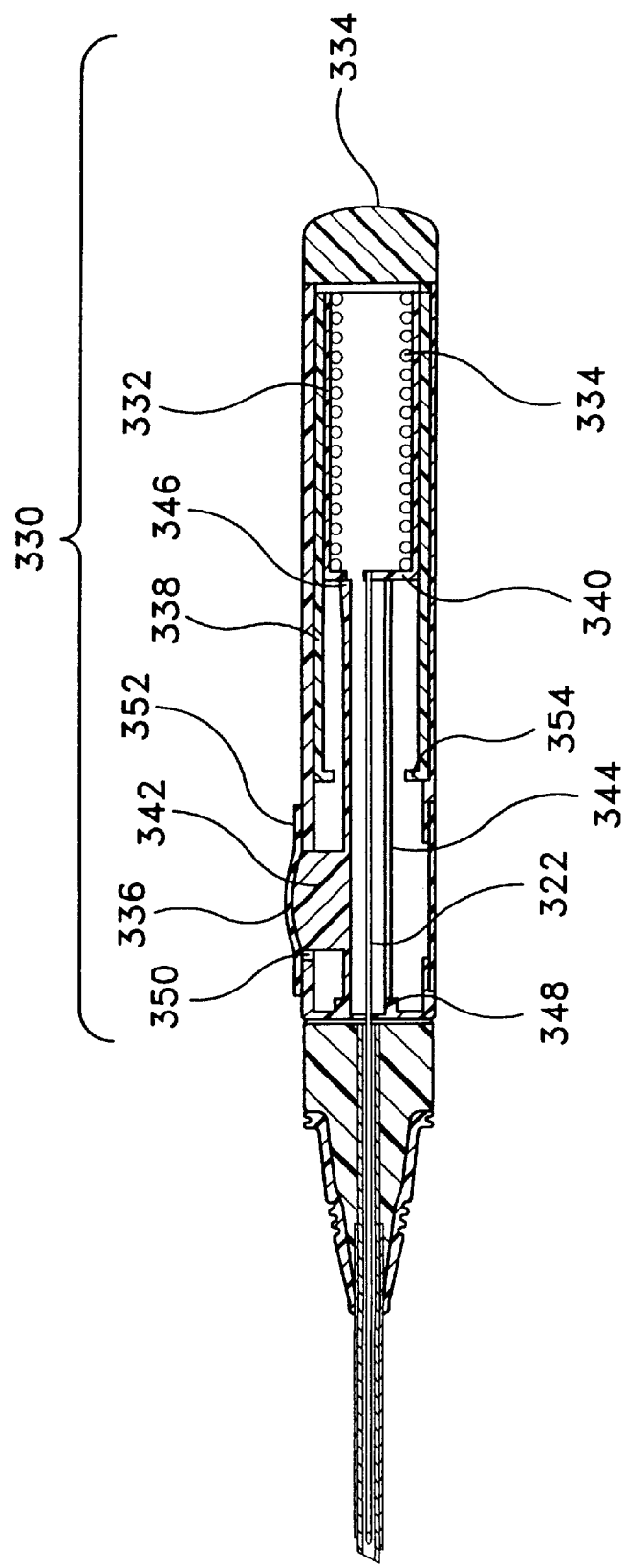
FIG. 8 is a cross sectional view of an alternative embodiment of the vascular access device of the present invention in the locked position before the advancement of the guide wire.
Figure 9:
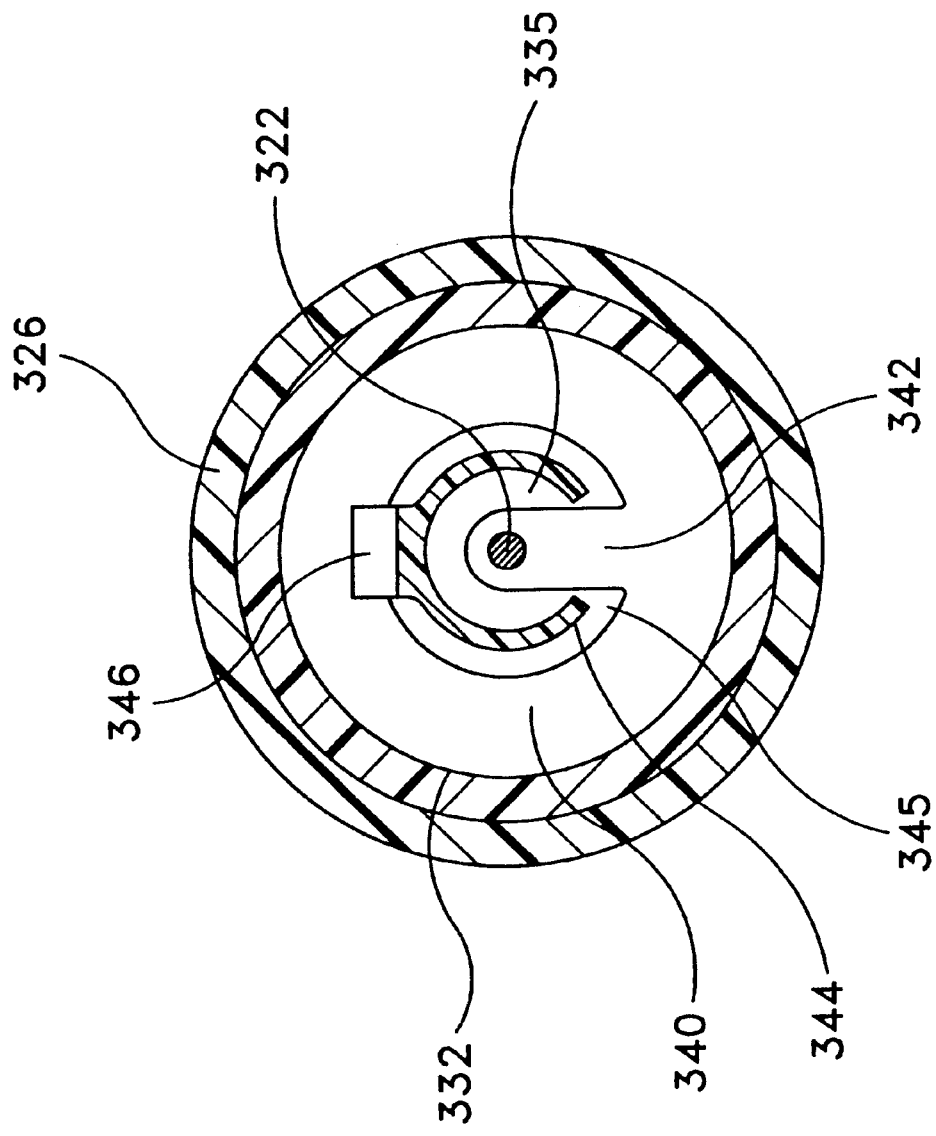
FIG. 9 is a cross sectional view taken along line 9—9 illustrated in FIG. 8.

FIGS. 8 and 9 illustrate yet another embodiment of the present invention which employs an alternative means of advancing guide wire 322 into a patient's blood vessel. In FIG. 8, vascular access device 310 has an actuating mechanism 330 generally comprising a plunger 332, a spring 334, a wire release mechanism 336 and a plunger track 338. Track 338 is a thin cylindrical tube attached to the inner wall of housing 326 by adhesive engagement, or other engagement well known in the art. One skilled in the art will appreciate, however, that track 338 and housing 326 can be molded from a single material. Track 338 extends from the proximal end of housing 326 near cap 334 distally up to or near release button 342 of wire release mechanism 336. It will be appreciated by one skilled in the art that the exact length of track 338 and housing 326 may be varied depending on the distance that guide wire 322 is to be inserted into the patient's blood vessel.

Plunger 332 is disposed within and capable of moving axially along track 338. The relative configuration of plunger 302 and spring 334 is as in FIG. 6 except that the distal face of plunger 332 has a rim 340, a tab 342, and a blood bypass hole 335. Spring 334, disposed within plunger 332, is delimited proximately by cap 334 and distally by rim 340 of plunger 332. As best illustrated in FIG. 9, blood bypass-hole 335 forms tab 342 and prevents flashback blood from being reintroduced into the artery by plunger 372 as it advances distally through cavity 336. In addition, as will explained below, blood bypass hole 335 accommodates beam 344 as plunger 332 advances distally along track 338. Guide wire 322 is attached by adhesive, threaded or friction engagement to tab 342. From tab 342, guide wire 322 extends distally through cavity 336, socket 348 and introducer needle 312.

When actuating mechanism 330 is in a locked position, plunger 332 and spring 334 are held in abeyance by guide wire release mechanism 336 disposed with cavity 336 of housing 326. Guide wire release mechanism 336 comprises a release button 342, a beam 344 and a release pawl 346. Beam 344 is attached to the distal end of housing 326 near nose 328 by threaded friction or adhesive engagement with socket 348 which is attached to and centered over the proximal end of nose 328. For reasons explained below, beam 344 has an opening 345 and is made of plastic, metal or other resilient material. From socket 348, beam 344 extends proximally to the distal face of plunger 332. Prior to initiation, release pawl 346 at the proximal end of beam 344 overlaps rim 340 on the distal face of plunger 332 preventing plunger 332 from advancing distally on track 338. At the distal end of beam 344, and in the same orientation as release pawl 346, is attached a release button 342. Release button 342 is positioned such that it protrudes from housing 326 through slit 350 and pushes against elastomeric band 352. The resilient force of beam 344 ensures that release button 342 remains biased against elastomeric band 352.

In practice, introducer needle 312 is first inserted into the blood vessel. Once in the blood vessel, the clinician initiates actuating mechanism 330 by depressing release button 342 through elastomeric band 352. The downward force on release button 342 causes beam 344 to bend, forcing release pawl 346 downward and away from rim 340 of plunger 332. When release pawl 346 no longer overlaps rim 340, the resilient force of spring 334 against cap 334 advances plunger 332 and guide wire 322 distally on track 338. As plunger 332 advances distally, beam 344 and release pawl 346 pass through blood bypass hole 335 on the distal face of plunger 332 and the center of spring 334. Tab 342 advances down the center of beam 344 through opening 345. Should guide wire 322 fail to fully advance for any reason, the clinician can reset actuating mechanism 330 by disengaging cap 334 from housing 326 and pulling cap 334 proximally until pawl 346 engages rim 340 on the face of plunger 332.

Blood bypass hole 335 in the distal face of plunger 332 allows flash back blood to pass through plunger 332 as it advances distally on track 338. Thus, the flash back blood is not reintroduced back into the patient's blood vessel. Plunger 332 comes to rest and guide wire 322 ceases to advance when rim 340 reaches abutment 354 of track 338. Once guide wire 322 has ceased to advance and is in position within the patient's blood vessel, catheter 316 is inserted and guide wire 322 and introducer needle 312 is removed as explained above.

Thus, the present invention overcomes some significant limitations of the existing art. The present invention provides a vascular access device which automatically advances a guide wire into a blood vessel to facilitate that placement of a vascular catheter. The guide wire is advanced at a steady and consistent rate, and can be reset if necessary. The present invention allows for the insertion of the guide wire by use of one hand. This allows the operator to carefully and accurately place the catheter in the subject blood vessel. Thus, the present invention represents an advancement in the art of catheter placement.

What is claimed and desired to be secured by a united states letters patent is:

1. A vascular access device for introducing a catheter into a blood vessel of a patient comprising:
    a housing having a proximal end and a distal end;
    an introducer needle having a proximal end and a distal end, the proximal end of the introducer needle being attached to the distal end of said housing, the introducer needle being substantially hollow and having a tip at its distal end;
    a flexible wire having a proximal end and a distal end, the proximal end secured within said housing and the distal end extending within the introducer needle;
    actuating means disposed within said housing for advancing the flexible wire beyond the tip of the introducer needle and into the blood vessel, wherein the actuating means comprises a spring, a disk and a trigger, and wherein the spring is attached to the disk and the disk is attached to the flexible wire, wherein the expansion of the spring is capable of being prevented by the force of the trigger against the disk; and
    means for receiving a catheter such that said catheter is concentrically fitted over the introducer needle and secured to said housing.

2. A vascular access device as defined in claim 1 wherein said means for receiving a catheter comprises a nose secured to the distal end of said housing.

3. A vascular access device as defined in claim 1 wherein said housing is substantially cylindrical in shape.

4. A vascular access device as defined in claim 1 wherein the trigger further comprises a trigger arm, a trigger pin, and a trigger shaft, and wherein the trigger shaft engages the disk selectively preventing the expansion of the spring, the actuating means being initiated by depressing the trigger arm wherein the trigger pivots about the trigger pin thus disengaging the trigger shaft from the disk permitting the spring to expand and advancing the wire.

5. A vascular access device for introducing a catheter into a blood vessel of a patient comprising:
    a housing having a proximal end and a distal end;
    an introducer needle connected to the housing;
    a wire movably secured within the housing;
    a plunger disposed within the housing connected to the wire;
    a resilient member disposed within the housing and engaging the plunger; and
    a pivotable lever which engages the plunger and prevents the resilient member from advancing the plunger axially in a first position and which pivots to a second position to disengage from the plunger to propel the wire past the beveled tip of the introducer needle and into the blood vessel.

6. A vascular access device as defined in claim 5 wherein the plunger further comprises a hub and a plurality of spokes converging on the hub, and wherein the wire is attached to the hub, the spokes causing the plunger and the wire to spiral as the plunger advances axially within the housing.

7. A vascular access device for introducing a catheter into a blood vessel comprising:
    a housing having a proximal end and a distal end, a nose connected to the distal end of the housing;
    a hollow introducer needle having a tip and being attached to the nose;
    a catheter concentrically fitted over the introducer needle and engaged with the nose; and
    a guide wire actuating mechanism comprising:
        a resilient member;
        a disk attached to the resilient member;
        a guide wire attached to the disk and extending into the hollow introducer needle; and
        trigger means for selectively releasing said resilient member such that such guide wire is advanced past the tip of said needle.

8. A vascular access device as defined in claim 7 said trigger means comprising a shaft wherein the shaft engages the disk and selectively prevents the resilient member from expanding and propelling the guide wire past the beveled tip of the introducer needle and into the blood vessel.

9. A vascular access device as defined in claim 7 wherein the resilient member is a spring.

10. A vascular access device for introducing a catheter into a blood vessel comprising: a housing with a proximal end and a distal end, a nose connected to the distal end of the housing, a hollow introducer needle with a beveled tip attached to the nose, a catheter concentrically fitted over the introducer needle and engaged with the nose, and a guide wire actuating mechanism having a plunger having a face disposed within the housing;

a resilient member disposed within the plunger;

a guide wire attached to the face of the plunger; and a beam attached to the housing, the beam engaging the plunger face thus preventing the resilient member from advancing the plunger distally within the housing and propelling the guide wire past the beveled tip of the introducer needle and into the blood vessel.

11. A vascular access device as defined in claim 10 wherein the beam further comprises a pawl and the plunger face further comprises a rim, the pawl engaging the rim and preventing the resilient member from advancing the plunger distally within the housing.

12. A vascular access device as defined in claim 11 wherein the actuating mechanism further comprises a release button attached to the beam, downward force on the release button causing the beam to bend forcing the release pawl to move away from the rim and allowing the plunger to distally advance within the housing.

13. The vascular access device for introducing a catheter into a blood vessel of claim 12 wherein the actuating mechanism comprises a track on which the plunger advances distally within the housing.

14. The vascular access device for introducing a catheter into a blood vessel of claim 12 wherein the housing further comprises a slit and a elastomeric band, the release button positioned on the beam such that it protrudes the housing through the slit and pushes against the elastomeric band.

15. The vascular access device for introducing a catheter into a blood vessel of claim 14 wherein the plunger face further comprises a tab to which guide wire is attached and the beam further comprises an opening, the tab of the plunger passing through the opening in the beam as the plunger advances distally on the track.

16. The vascular access device for introducing a catheter into a blood vessel of claim 15 wherein the plunger face further comprises a blood bypass hole which allows flash back blood to pass through the plunger as it advances distally on the track.

17. The vascular access device for introducing a catheter into a blood vessel of claim 10 where the housing has a cap, the resilient member attached to the cap thus permitting the actuating mechanism to be set or reset in a locked position.

18. The vascular access device for introducing a catheter into a blood vessel of claim 10 wherein the resilient member is a spring.

\* \* \* \* \*